US009476049B2

(12) United States Patent
Hegele et al.

(10) Patent No.: US 9,476,049 B2
(45) Date of Patent: Oct. 25, 2016

(54) GUANOSINE-RICH OLIGONUCLEOTIDE (GRO) COMPOSITIONS, METHODS AND USES FOR TREATING RESPIRATORY SYNCYTIAL VIRUS INFECTION

(71) Applicants: THE GOVERNING COUNCIL OF THE UNIVERSITY OF TORONTO, Toronto (CA); HOSPITAL FOR SICK CHILDREN, Toronto (CA)

(72) Inventors: Richard George Hegele, Toronto (CA); Peter Mastrangelo, Etobicoke (CA); Theo Moraes, Toronto (CA)

(73) Assignees: THE GOVERNING COUNCIL OF THE UNIVERSITY OF TORONTO, Toronto (CA); HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 14/379,185

(22) PCT Filed: Feb. 15, 2013

(86) PCT No.: PCT/CA2013/050123

§ 371 (c)(1),
(2) Date: Aug. 15, 2014

(87) PCT Pub. No.: WO2013/131182

PCT Pub. Date: Sep. 12, 2013

(65) Prior Publication Data

US 2015/0010618 A1 Jan. 8, 2015

Related U.S. Application Data

(60) Provisional application No. 61/599,653, filed on Feb. 16, 2012.

(51) Int. Cl.
*C12N 15/113* (2010.01)
*A61K 31/711* (2006.01)

(52) U.S. Cl.
CPC ......... *C12N 15/1131* (2013.01); *A61K 31/711* (2013.01); *C12N 2310/16* (2013.01)

(58) Field of Classification Search
None
See application file for complete search history.

(56) References Cited

U.S. PATENT DOCUMENTS

| | | | | |
|---|---|---|---|---|
| 2002/0076693 A1 | 6/2002 | Hovanessian et al. | | |
| 2004/0002457 A1 | 1/2004 | Hovanessian et al. | | |
| 2009/0131351 A1* | 5/2009 | Green et al. | ..................... | 514/44 |
| 2011/0178161 A1 | 7/2011 | Trent et al. | | |

FOREIGN PATENT DOCUMENTS

| | | |
|---|---|---|
| WO | WO 0061597 | 10/2000 |
| WO | WO 2005037323 | 4/2005 |
| WO | WO 2007044851 | 4/2007 |
| WO | WO 2009098464 | 8/2009 |
| WO | WO 2011123945 | 10/2011 |
| WO | WO 2011129495 | 10/2011 |
| WO | WO 2011133142 | 10/2011 |

OTHER PUBLICATIONS

Tayyari, Farnoosh, Identification of a novel receptor for human RSV, Thesis for UBC, online available 2008.*
Cucumis melo genomic chromosome, chr_7 printed Jun. 7, 2015.*
Anderson et al. (1985). Antigenic characterization of respiratory syncytial virus strains with monoclonal antibodies. J. Infect. Dis. 151, 626-633.
Behera et al. (2001). Blocking intercellular adhesion molecule-1 on human epithelial cells decreases respiratory syncytial virus infection. Biochem. Biophys. Res. Commun. 280, 188-195.
Bem et al. (2009). Mechanical ventilation enhances lung inflammation and caspase activity in a model of mouse pneumovirus infection. AJP—Lung Physiol. 296, L46-L56.
Cane P.A. (1997). Analysis of linear epitopes recognised by the primary human antibody response to a variable region of the attachment (G) protein of respiratory syncytial virus. J. Med. Virol. 51, 297-304.
Cane, P.A. (2001). Molecular epidemiology of respiratory syncytial virus. Rev. Med. Virol. 11:103-.
Cane, P.A. and Pringle, C.R. (1995). Evolution of subgroup A respiratory syncytial virus: evidence for progressive accumulation of amino acid changes in the attachment protein. J. Virol. 69, 2918-2925.
Chen et al. (2008). Cell surface nucleolin serves as receptor for DNA nanoparticles composed of pegylated polylysine and DNA. Mol. Ther. 16, 333-342.
Coates et al. (1966). An antigenic analysis of respiratory syncytial virus isolates by a plaque reduction neutralization test. Am. J. Epidemiol. 83, 299-313.
Collins, P.L. & Graham, B.S. (2008). Viral and host factors in human respiratory syncytial virus pathogenesis. J Virol. 82, 2040-2055.
Dapic, V. et al. (2002) Antiproliferative activity of G-quartet-forming oligonucleotides with backbone and sugar modifications. Biochemistry 41: 3676-85.
Dapic, V. et al. (2003) Biophysical and biological properties of quadruplex oligodeoxyribonucleotides. Nucleic Acids Res 31: 2097-107.
Domachowske, J.B. and Rosenberg, H.F. (1999). Respiratory syncytial virus infection: immune response, immunopathogenesis, and treatment. Clinical Microbiol. Rev. 12, 298-309.
Escobar, G.J., et al. (2010). Recurrent wheezing in the third year of life among children born at 32 weeks' gestation or later: relationship to laboratory-confirmed, medically attended infection with respiratory syncytial virus during the first year of life. Arch. Pediatr. Adolesc. Med. 164, 915-922.
Feldman et al. (2000). The fusion glycoprotein of human respiratory syncytial virus facilities virus attachment and infectivity via an interaction with cellular heparan sulfate. J. Virol. 74, 6442-6447.

(Continued)

*Primary Examiner* — Shanon A Foley
*Assistant Examiner* — Myron Hill

(57) ABSTRACT

Provided herein is a method of treating Respiratory Syncytial Virus (RSV) infection in a cell. The method involves administering the guanosine-rich oligonucleotide (GRO) AS 1411 (5'-GGTGGTGGTGG TTGTGGTGGTGGTGG-3'—also known as GR026B and AGRO100) to the cell.

10 Claims, 11 Drawing Sheets

(56) References Cited

OTHER PUBLICATIONS

Garcia et al. (1994). Evolutionary patterns of human respiratory syncytial virus (subgroup A): cocirculating lineages and correlation of genetic and antigenic changes in the G glycoprotein. J. Virol. 68, 5448-5459.
Garcia-Barreno et al. (1998). Marked differences in the antigenic structure of human respiratory syncytial virus F and G glycoproteins. J. Virol. 63, 925-932.
Hall, C.B., et al. (2009). The burden of respiratory syncytial virus infection in young children. N. Engl. J. Med. 360, 588-598.
Hallak et al. (2000). Glycosaminoglycan sulfation requirements for respiratory syncytial virus infection. J. Virol. 74, 10508-10513.
Hallak, L.K., Kwilas, S.A. & Peeples, M.E. (2007). Interaction between respiratory syncytial virus and glycosaminoglycans, including heparan sulfate. Methods Mol Biol 379, 15-34.
Hegele, R.: "Making sense of cell surface nucleolin: Implications for respiratory syncytial virus prophylaxis and theraoy" Cell Cycle, vol. 11, No. 1, Jan. 1, 2012 (Jan. 1, 2012) pp. 1-2.
Hendry et al. (1986). Concurrent circulation of antigenically distinct strains of respiratory syncytial virus during community outbreaks. J. Infect. Dis. 153, 291-297.
Johnson et al. (1987). The G glycoprotein of human respiratory syncytial viruses of subgroups A and B: extensive sequence divergence between antigenically related proteins. Proc. Natl. Acad. Sci. USA 84, 5625-5629.
Johnson et al. (2007). The histopathology of fatal untreated human respiratory syncytial virus infection. Mod. Pathol. 20, 108-119.
Kaan, P.M. and Hegele R.G. (2003). Interaction between respiratory syncytial virus and particulate matter in guinea pig alveolar macrophages. Am. J. Respir. Cell. Mol. Biol. 28, 697-704.
Krusat, T. and Streckert, H.J. (1997). Heparin-dependent attachment of respiratory syncytial virus (RSV) to host cells. Arch. Virol. 142, 1247-1254.
Malhotra et al. (2003). Isolation and characterisation of potential respiratory syncytial virus receptor(s) on epithelial cells. Microbes Infect 5, 123-133.
Marsh, M. and Helenius, A. (2006). Virus Entry: Open Sesame. Cell 124, 729-740.
Mastrangelo, P. and Hegele, R. G. The RSV fusion receptor: not what everyone expected it to be. Microbes and INfection, issue of Nov. 2012 (Nov. 2012) vol. 14, No. 13, pp. 1205-1210, ISSN 1286-4579. Section 5.2.
Mufson et al. (1985). Two distinct subtypes of human respiratory syncytial virus. J. Gen. Virol. 66.
Nisole et al. (1999). The anti-HIV pseudopeptide HB-19 forms a complex with the cell-surface-expressed nucleolin independent of heparan sulfate proteoglycans. J. Biol. Chem. 274, 27875-84.
Peret et al. (1998). Circulation patterns of genetically distinct group A and B strains of human respiratory syncytial virus in a community. J. Gen. Virol. 79, 2221-2229.
Rueda et al. (1991). Premature stop codons in the G glycoprotein of human respiratory syncytial viruses resistant to neutralization by monoclonal antibodies. J. Virol. 65, 3374-3378.
Sullender et al. (1991). Genetic diversity of the attachment protein of subgroup B respiratory syncytial viruses. J. Virol. 65, 5425-5434.
Sullender et al. (1993). Analysis of respiratory syncytial virus genetic variability with amplified cDNAs. J. Clin. Microbiol. 31, 1224-1231.
Tayyari, F. et al. (2011). Identification of nucleolin as a cellular receptor for human respiratory syncytial virus. Nat Med. 17(9):1132-5.
Techaarpornkul, S., Barretto, N. & Peeples, M.E. (2001). Functional analysis of recombinant respiratory syncytial virus deletion mutants lacking the small hydrophobic and/or attachment glycoprotein gene. J. Virol. 75, 6825-6834.
Techaarpornkul, S., Collins, P.L. & Peeples, M.E. (2002). Respiratory syncytial virus with the fusion protein as its only viral glycoprotein is less dependent on cellular glycosaminoglycans for attachment than complete virus. Virology 294, 296-304.
Tuteja et al. (1998). Nucleolin: a multifunctional major nucleolar phosphoprotein. Crit. Rev. Biochem. Mol. Biol. 33, 407-436.
Wu, H., Pfarr, D.S., Losonsky, G.A. & Kiener, P.A. (2008). Immunoprophylaxis of RSV infection: advancing from RSV-IGIV to palivizumab and motavizumab. Curr Top Microbiol Immunol 317, 103-123.
Zhang, L., Peeples, M.E., Boucher, R.C., Collins, P.L. & Pickles, R.J. (2002). Respiratory syncytial virus infection of human airway epithelial cells is polarized, specific to ciliated cells, and without obvious cytopathology. J Virol 76, 5654-5666.

* cited by examiner

A B

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: synthetic

<400> SEQUENCE: 1
ggtggtggtg gttgtggtgg tggtgg 26

<210> SEQ ID NO 2
<211> LENGTH: 710
<212> TYPE: PRT
<213> ORGANISM: Homo sapiens

<400> SEQUENCE: 2

```
Met Val Lys Leu Ala Lys Ala Gly Lys Asn Gln Gly Asp Pro Lys Lys
1               5                   10                  15

Met Ala Pro Pro Pro Lys Glu Val Glu Glu Asp Ser Glu Asp Glu Glu
            20                  25                  30

Met Ser Glu Asp Glu Glu Asp Asp Ser Ser Gly Glu Glu Val Val Ile
        35                  40                  45

Pro Gln Lys Lys Gly Lys Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
    130                 135                 140

Ser Asp Glu Glu Glu Asp Asp Asp Ser Glu Glu Asp Glu Glu Asp Asp
145                 150                 155                 160
```

-continued

```
Glu Asp Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Asp Glu Glu Asp Asp Ser Glu Glu
        195                 200                 205

Glu Ala Met Glu Thr Thr Pro Ala Lys Gly Lys Lys Ala Ala Lys Val
    210                 215                 220

Val Pro Val Lys Ala Lys Asn Val Ala Glu Asp Glu Asp Glu Glu Glu
225                 230                 235                 240

Asp Asp Glu Asp Glu Asp Asp Asp Asp Asp Glu Asp Asp Glu Asp Asp
                245                 250                 255

Asp Asp Glu Asp Asp Glu Glu Glu Glu Glu Glu Glu Glu Glu Glu Pro
            260                 265                 270

Val Lys Glu Ala Pro Gly Lys Arg Lys Lys Glu Met Ala Lys Gln Lys
        275                 280                 285

Ala Ala Pro Glu Ala Lys Lys Gln Lys Val Glu Gly Thr Glu Pro Thr
    290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
        355                 360                 365

Leu Lys Val Phe Gly Asn Glu Ile Lys Leu Glu Lys Pro Lys Gly Lys
    370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Glu Lys Thr Phe Glu Glu
        435                 440                 445

Lys Gln Gly Thr Glu Ile Asp Gly Arg Ser Ile Ser Leu Tyr Tyr Thr
    450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
        515                 520                 525

Glu Phe Ala Ser Phe Glu Asp Ala Lys Glu Ala Leu Asn Ser Cys Asn
    530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
```

-continued

```
            580                 585                 590

Asp Gly Ser Val Arg Ala Arg Ile Val Thr Asp Arg Glu Thr Gly Ser
        595                 600                 605

Ser Lys Gly Phe Gly Phe Val Asp Phe Asn Ser Glu Glu Asp Ala Lys
    610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
                645                 650                 655

Gly Gly Gly Arg Gly Gly Phe Gly Gly Arg Gly Gly Gly Arg Gly Gly
            660                 665                 670

Arg Gly Gly Phe Gly Gly Arg Gly Arg Gly Gly Phe Gly Gly Arg Gly
        675                 680                 685

Gly Phe Arg Gly Gly Arg Gly Gly Gly Gly Asp His Lys Pro Gln Gly
    690                 695                 700

Lys Lys Thr Lys Phe Glu
705                 710


<210> SEQ ID NO 3
<211> LENGTH: 26
<212> TYPE: DNA
<213> ORGANISM: Artificial Sequence
<220> FEATURE:
<223> OTHER INFORMATION: synthetic

<400> SEQUENCE: 3

cctcctcctc cttctcctcc tcctcc                                          26
```

GUANOSINE-RICH OLIGONUCLEOTIDE (GRO) COMPOSITIONS, METHODS AND USES FOR TREATING RESPIRATORY SYNCYTIAL VIRUS INFECTION

CROSS REFERENCE TO RELATED APPLICATIONS

The present application is a national phase entry under 35 U.S.C. §371 of International Application no. PCT/CA2013/050123 filed Feb. 15, 2013, published in English, which claims priority from U.S. Provisional Application 61/599,653 filed Feb. 16, 2012, all of which are hereby incorporated by reference.

TECHNICAL FIELD

The invention is in the field of treatment of Respiratory Syncytial Virus (RSV) infection, and particularly methods, uses, and guanosine-rich oligonucleotide (GRO) compositions for treating RSV infection.

BACKGROUND

Human respiratory syncytial virus (RSV) is an enveloped, single-stranded, negative-polarity RNA *Pneumovirus* of the family Paramyxoviridae. It is a common cause of respiratory tract infections worldwide, including bronchiolitis and other serious illnesses (see, for e.g., Collins and Graham, 2008; Wu et al., 2008). Control and prevention of RSV infection is a global health priority; almost all children are infected with RSV during the first two years of life (see, for e.g., Domachowske and Rosenberg, 1999). In the United States alone, over 2 million RSV-infected infants require medical attention annually (Hall et al., 2009). Infants hospitalized for RSV are also at risk for developing recurrent wheezing and asthma (Escobar et al., 2010).

Polarized, ciliated respiratory epithelial cells are a major target for RSV infection in vivo (see, for e.g., Johnson et al., 2007). RSV infection of ciliated respiratory epithelial cells in vitro occurs on the apical (luminal) aspect (see, for e.g., Zhang et al., 2002). Viral replication in a host cell initiates with attachment of the virus to the plasma membrane via receptor-mediated binding (see, for e.g., Marsh and Helenius, 2006). Candidate RSV receptors have been proposed (see, for e.g., Krusat and Streckert, 1997; Behera et al., 2001; and, Malhotra et al., 2003). Laboratory-adapted strains of RSV show increased efficiency of infection by binding to cell surface glycosaminoglycans (GAGs); however, cells deficient in GAGs are permissive to infection (see, for e.g., Feldman et al., 2000) and the role of GAGs in cellular infection by wild-type, community isolates of RSV is unclear (see, for e.g., Hallak et al., 2007).

Options for treatment are limited, vaccination poses numerous obstacles, and passive prophylactic treatment using anti-RSV antibodies (e.g., palivizumab) is expensive, is not 100% effective, and is limited to those at high risk for severe infection (Wu et al., 2008).

The RSV envelope contains three proteins: small hydrophobic (SH), glycoprotein (G) and fusion (F) (Collins and Graham, 2008). SH protein is not required for virus binding (see, for e.g., Techaarpornkul et al., 2001). RSV G, the heterogeneity of which characterizes RSV subtypes A and B, binds to cell surface glycosaminoglycans (GAGs) at high affinity (see, for e.g., Hallak et al., 2007), but is not an absolute requirement for infection, since mutant RSV deficient in G glycoprotein (RSV ÄG) remains infectious (see, for e.g., Techaarpornkul et al., 2002). Moreover, cells deficient in cell surface GAGs or with chemically modified GAGs are permissive to RSV, albeit at lower levels than cells expressing abundant GAGs (see, for e.g., Techaarpornkul et al., 2002; and Hallak et al., 2000).

Nucleolin is a ubiquitous nucleolar phosphoprotein involved in fundamental aspects of transcription regulation, cell proliferation and growth (see, for e.g., Tuteja et al., 1998; and Chen et al., 2008). Nucleolin has also been described as a shuttling molecule between nucleus, cytosol and the cell surface. Studies have demonstrated that surface nucleolin may serve as a receptor for various extracellular ligands, for instance those implicated in cell proliferation, differentiation, adhesion, mitogenesis and angiogenesis. Nisole et al. (1999), US20040002457A1, and US20020076693A1 disclose that nucleolin is involved in binding of HIV virus to host cells. Nucleolin peptide, nucleotide antibodies, and nucleolin RNAi have all been shown used for inhibiting RSV infection (WO/2011/123945).

SUMMARY

The present invention is based in part on the discovery that nucleolin plays a role in RSV infection, and that the administration of guanosine-rich oligonucleotide (GRO) AS1411-5'-GGTGGTGGTGG TTGTGGTGGTGGTGG-3' (SEQ ID No: 1) (also known as GR026B and AGRO100) to a cell may be useful in the treatment of RSV infection. Such a treatment may cause interference with the interaction between RSV protein F and a cells endogenous nucleolin.

In a first aspect, a method is provided for of treating Respiratory Syncytial Virus (RSV) infection in a cell, the method including administering AS1411 to the cell.

In a further aspect, there is provided a use of AS1411 having a sequence of SEQ ID NO:1 for the treatment of RSV infection.

In a further aspect, there is provided a use of AS1411 having a sequence of SEQ ID NO:1 in the preparation of a medicament for the treatment of RSV infection.

In a further aspect, AS1411 is provided for of treating Respiratory Syncytial Virus (RSV) infection in a cell.

In a further aspect, there is provided a commercial package, comprising: (a) AS1411; and (b) instruction for use in the treatment of RSV.

The cell may be a human cell. The human cell may be an epithelial cell. The human cell may be a mucosal cell. The human cell may be a cell of the respiratory tract. The human cell may be a ciliated respiratory epithelial cell. The cell may be in a subject having or at risk of developing an RSV infection. The AS1411 molecule may be administered intravenously. The AS1411 molecule may be topically administered to a mucosal membrane of the subject. The AS1411 molecules may be mixed with lipid particles prior to administration. The AS1411 molecules may be encapsulated in liposomes prior to administration. The AS1411 molecule may also be administered via nasal spray or intramuscularly or intravenously.

The treatment may be of a human subject. The treatment may be of a bovine subject. The treatment may be of an ovine subject. The treatment may be of an equine subject. The treatment may be of a porcine subject. The treatment may be of a murine subject.

The RSV may be a human strain of RSV. The RSV may be a bovine strain of RSV. The RSV may be an ovine strain of RSV. The RSV may be an equine strain of RSV. The RSV may be a porcine strain of RSV.

DETAILED DESCRIPTION

Figure 1:
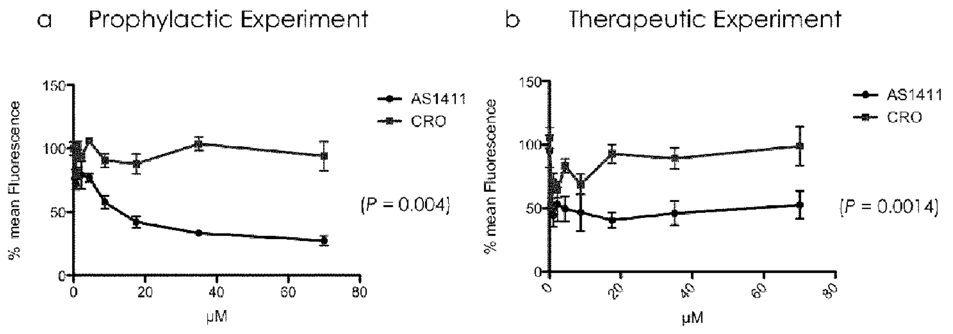
FIG. 1*a* shows a graph of fluorescence signal over a wide dosing range of AS1411 and CRO (control) in RSV-infected HEp-2 cells, where the cells were pre-treated with oligo (prophylactic experiment) 24 hrs before exposure to RSV (MOI=1.0).
FIG. 1*b* shows a graph of fluorescence signal over a wide dosing range of AS1411 and CRO (control) in RSV-infected HEp-2 cells, where the cells were exposed to RSV 24 hrs (MOI=0.1) before adding the oligo (therapeutic experiment).

Any terms not directly defined herein shall be understood to have the meanings commonly associated with them as understood within the present field of art. Certain terms are discussed below, or elsewhere in the specification, to provide additional guidance to the practitioner in describing the compositions, devices, methods and the like of embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments described herein.

A method is provided for "treating" Respiratory Syncytial Virus (RSV) infection in a cell, wherein treating is meant to encompass preventing RSV infection, ameliorating RSV infection, and eradicating RSV infection. The term "treating" as used herein is also meant to include the prophylactic administration of a compound prior to infection of RSV or in anticipation of RSV infection, the administration of a compound when there is an ongoing infection with RSV, or if the RSV is in a latent state. Those skilled in the art would appreciate that the term "preventing" would include the avoidance of infection with RSV or minimizing RSV infection once an exposure to RSV occurs. A person of skill in the art would appreciate that the term "ameliorating" is meant to include the prospect of making an infection more tolerable for a subject afflicted with an RSV infection (for example, by reducing viral load in a subject). A person of skill in the art would also appreciate that the term "eradication" with regards to RSV infection would include elimination of the RSV from a subject or removal of the infection (for example by the treatment itself or in conjunction with another treatment(s) and/or the subjects immune response). Accordingly, as used herein "treatment" may refer to the prevention of an RSV infection, the amelioration of an RSV infection, the eradication of RSV from a subject, or combinations thereof. Furthermore, a "treatment" may be prophylactic, whereby the treatment is administered prior to infection or the appearance of symptoms in a subject or in anticipation of an exposure to RSV. Similarly, "treatment" may be administered following RSV infection or the onset of RSV infection symptoms.

As used herein, the term "RSV" refers to Respiratory Syncytial Virus, which is an enveloped, single-stranded, negative-polarity RNA *Pneumovirus* of the family Paramyxoviridae. Human RSV strains are significant causes of bronchiolitis and other serious lower respiratory tract infections worldwide, especially in children, the elderly, and in immunocompromised adults. The term RSV may include, without limitation, respiratory syncytial viruses of the *Pneumovirus* genus which have specificity for other host species, such as bovine respiratory syncytial virus, ovine respiratory syncytial virus and murine pneumonia virus, which is also known in the art as PVM (see, for e.g., Bem et al., 2009). As used herein, the term "infection" refers to a state in which an infectious agent, such as a virus, and including without limitation RSV, is established within a cell or within a subject, as the case may be. In certain embodiments, the compounds may be used for treating RSV infection. Such methods and compounds are described herein.

Human RSV strains may be classified as A or B group viruses (i.e., RSV-A and RSV-B) based on MAb binding to the RSV glycoprotein (G protein) (see, for e.g., (Anderson et al., 1985; Coates et al., 1966; Hendry et al., 1986; Mufson et al., 1985) and by genetic analysis (see, for e.g., Garcia et al., 1994; Sullender et al., 1991; Sullender et al., 1993). The RSV G protein is thought to be the most variable of the RSV proteins (see, for e.g., Garcia-Barreno et al., 1989; Johnson et al., 1987; Mufson et al., 1985), and its C-terminal region (the second hypervariable region) accounts for strain-specific epitopes (see, for e.g., Cane, 1997; Cane, 2001; Cane and Pringle, 1995; Garcia et al., 1994; Johnson et al., 1987; Peret et al., 1998; Rueda et al., 1991). By contrast the F protein of RSV is much less variable between strains and is thus a more attractive target for a broad based RSV treatment.

Nucleolin is a ubiquitous nucleolar phosphoprotein involved in fundamental aspects of transcription regulation, cell proliferation and growth (see, for e.g., Tuteja et al., 1998; and Chen et al., 2008). Nucleolin has also been described as a shuttling molecule between nucleus, cytosol and the cell surface. Studies have demonstrated that surface nucleolin may serve as a receptor for various extracellular ligands, for instance those implicated in cell proliferation, differentiation, adhesion, mitogenesis and angiogenesis.

The term “nucleolin” refers, in part, to the polypeptide expression product of the nucleolin gene, the human orthologue corresponding to EntrezGene #4691, GenPept Protein Accession #P19338.3. Homologous nucleolin proteins are found in other species which bear sequence similarity to human nucleolin and may thus find utility herein, including but not limited to mouse (EntrezGene #17975; GenPept #P09405.2), Guinea Pig (EntrezGene #100735210; GenPept #XP_003474646) and rat (EntrezGene #25135; GenePept #P13383.3). The term “nucleolin” also refers to the nucleolin gene itself, and includes reference to the nucleolin gene as it is present in a variety of genomes including, without limitation, human, bovine, ovine, equine, porcine, and murine. The term “nucleolin” also includes gene products (e.g., mRNA, protein) produced from the underlying nucleolin gene. It will be appreciated by a person skilled in the art that the term “nucleolin peptide” qualifies the understanding of the term “nucleotide” by making specific reference to a “peptide” as it is defined herein. For example, SEQ ID NO:2 provides an amino acid sequence of human nucleolin. The term “nucleolin” also includes post-translationally modified forms of the protein.

Active GROs have been shown to bind to cell surface Nucleolin and are often referred to as “Nucleolin aptamers.” Encompassed herein is the use of a guanosine-rich oligonucleotide (GRO) called AS1411 for administration to a cell. AS1411 (as described in WO2009098464) has the sequence 5'-GGTGGTGGTGGTTGTGGTGGTGGTGG-3' (SEQ ID No: 1) and is also known as GR026B and AGRO100. AS1411 is a 26-mer DNA aptamer, which is currently undergoing clinical evaluation in acute myeloid leukemia (AML). AS1411 is a guanine-rich aptamer has unmodified phosphodiester linkages and forms a G-quadruplex structure (Dapic, V. et al. 2003) that is resistant to degradation by serum enzymes (Dapic, V. et al. 2002). AS1411 shows high affinity and specificity for nucleolin.

Since the identification of Nucleolin as a receptor for RSV infection (Tayyari, F. et al., 2011) AS1411 was tested for an effect on RSV infection using a fluorescence focus assay (FFA). In FFA, the amount of infected cells per well after 24 hrs exposure to the virus is converted to a fluorescent signal.

The compounds, as described herein, may be in isolation, or may be linked to or in combination with tracer compounds, liposomes, carbohydrate carriers, polymeric carriers or other agents or excipients as will be apparent to one of skill in the art. In alternate embodiments, such compounds may further comprise an additional medicament, wherein such compounds may be present in a pharmacologically effective amount.

The term “medicament” as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a, mouse, rat, dog, cat, cow, sheep, horse, hamster, guinea pig, rabbit, cotton rat, or pig. The medicament may be comprised of the effective chemical entity alone or in combination with a pharmaceutically acceptable excipient.

The term “pharmaceutically acceptable excipient” may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Compositions or compounds according to some embodiments described herein may be administered in any of a variety of known routes. Examples of methods that may be suitable for the administration of a compound include orally, intravenous, inhalation, intramuscular, subcutaneous, topical, intraperitoneal, intra-rectal or intra-vaginal suppository, sublingual, and the like. The compounds described herein may be administered as a sterile aqueous solution, or may be administered in a fat-soluble excipient, or in another solution, suspension, patch, tablet or paste format as is appropriate. A composition comprising the compounds described herein may be formulated for administration by inhalation. For instance, a compound may be combined with an excipient to allow dispersion in an aerosol. Examples of inhalation formulations will be known to those skilled in the art. Other agents may be included in combination with the compounds described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, “Remington's Pharmaceutical Sciences”, (19th edition), ed. A. Gennaro, 1995, Mack Publishing Company, Easton, Pa.

The dosage of the compositions or compounds of some embodiments described herein may vary depending on the route of administration (oral, intravenous, inhalation, or the like) and the form in which the composition or compound is administered (solution, controlled release or the like). Determination of appropriate dosages is within the ability of one of skill in the art. As used herein, an “effective amount”, a “therapeutically effective amount”, or a “pharmacologically effective amount” of a compound refers to an amount of the AS1411 present in such a concentration to result in a therapeutic level of the compound delivered over the term that the compound is used. This may be dependent on the mode of delivery, time period of the dosage, age, weight, general health, sex and diet of the subject receiving the compound. Methods of determining effective amounts are known in the art. It is understood that it could be potentially beneficial to restrict delivery of the compounds described herein to the target tissue or cell in which inhibition of RSV infection is desired. It is also understood that it may be desirable to target the compounds described herein to a desired tissue or cell type. The compounds described herein may thus be coupled to a targeting moiety. The compounds may be coupled to a cell uptake moiety. The targeting moiety may also function as the cell uptake moiety.

Methods and Materials

The following methods and materials were employed with respect to the Examples described herein.

Cells.

HEp-2 (product # is ATCC CCL-23) and MDCK cells (product number is ATCC CCL-34) were obtained from (American Type Culture Collection (ATCC), Rockville, Md.) were maintained in Dulbecco's modified essential medium (Invitrogen™, Carlsbad, Calif.) supplemented with 1% L-glutamine (Invitrogen™) and 10% (v/v) heat-inactivated fetal bovine serum (FBS) (Invitrogen™), at 37° C. All cell cultures were kept in a humidified incubator containing 5% $CO_2$.

Viruses.

Working stocks of RSV A2 and RSV B (ATCC), RSV lacking G protein (RSV ΔG) (gift of Dr. P. L. Collins, National Institutes of Health, Bethesda, Md.), RSV expressing GFP (Hallak et al., 2000) were prepared as previously described (Kaan and Hegele, 2003).

RSV Propagation (In Vivo Experiments).

Cells involved with RSV propagation were routinely screened for mycoplasma and LPS. $2\times10^7$ HEp-2 cells (ATCC) were seeded in 10% FBS EMEM in a T-150 tissue culture flask. Cells were left to grow in 37° C., 5% $CO_2$ incubator overnight. The next day (Day 0), cells were rinsed twice with clean PBS. RSV-A2 (ATCC) was added in 12 mL of serum free EMEM at an MOI~0.1. Cells/RSV underwent incubation for 2 to 4 h while rotating flask every 15 to 30 min. Twenty-eight mL 6% FBS EMEM were added to flasks and cells incubated for 3 to 4 days. By day 4, 50% cells usually detached and virus was harvested and purified.

RSV Harvesting and Purification.

Infected HEp-2 cells were scraped and collected with media into 50 mL Falcon tubes, and then underwent centrifugation at 820×g for 10 min. All solutions and cells were kept on ice or at 4° C. unless otherwise stated. Supernatant was decanted and placed in a cold 50 mL falcon tube. The cell pellet was resuspended with 5 mL medium, then quick frozen in liquid nitrogen, and melted at 37° C. with constant agitation. This freeze-thaw cycle was repeated once. The resuspended pellet underwent sonication on ice for 20 s twice and centrifugation at 820×g for 10 min. The cell pellet was discarded and the supernatant was combined with the original decanted media for ultracentrifugation (SW28 rotor) at 110,000×g for 45 min, over a sucrose cushion (30% sucrose in 0.1 M sodium chloride, 0.01 M Tris-HCl, 0.001 M EDTA, 1 M urea, pH=7.5). After this spin a virus pellet was clearly visible and supernatant was decanted and disposed. The pellet was resuspended in 100-150 μL LPS-free PBS per T-150 flask (yield: 2×108 PFU RSV/mL) and stored at −80° C. or in liquid nitrogen.

Aptamers.

A guanosine-rich oligonucleotide (GRO) called AS1411 having the sequence 5'-GGTGGTGGTGGTTGTGGTG-GTGGTGG-3' (SEQ ID No: 1) was used herein. As a negative control the same oligo, but with all the guanosines substituted with cytosine residues (CRO) 5'-CCTCCTC-CTCCTTCTCCTCCTCCTCC-3' (SEQ ID No: 3) was used. Others have already shown that CRO serves as a negative control for AS1411's anti-cancer cell activity. AS1411 and CRO were obtained from Life Technologies™.

Fluorescence Focus Assay (Malhotra et al., 2003): Briefly, HEp-2 cells cultured in EMEM supplemented with 10% foetal bovine serum (FBS) and antibiotics are plated onto black flat clear-bottomed 96 well plates ($1\times10^4$ cells/well). The next day virus is added and incubated for 24 hrs at 37° C. and 5% $CO_2$ to allow at least one full round of virus replication. The cells are then fixed with 75% cold acetone in PBS for 5 minutes. Following 3 washes with PBS/0.1% Tween-20™ (PBS-Tween) cells were incubated with a 1:10 dilution of NCL-RSV3 (Novacastra™; mouse anti-RSV monoclonal pool) in PBS-Tween/10% FBS for 30 minutes at room temperature. Cells were washed again as before and incubated with 1:400 dilution (5 μg/mL) of Alexa Fluor 488™ anti-mouse IgG (Life Technologies™) in PBS-Tween/10% FBS. After washing again as before with PBS-Tween, cells were counterstained with 0.1% naphthol blue black for 10 minutes at room temperature. Then, after a final washing, fluorescence was detected with a Tecan Infinite M200Pro™ plate reader (ex. 488 nm, em. 519 nm).

In this assay the amount of infected cells per well after 24 hrs exposure to RSV is converted to a fluorescent signal. AS1411 was applied to the wells in triplicate starting at 70 μM with serial dilutions down to 0.55 μM. As a negative control we used a derivative of the same compound that does not interact with Nucleolin (CRO). In "prophylactic" experiments we pre-treated cells with oligo 24 hrs before exposure to RSV (MOI=1.0). In "therapeutic" experiments we exposed cells to RSV (MOI=0.1) 24 hrs before adding the compound.

In experiments with MDCK cells, cells were plated at $4\times10^4$ cells/well and maintained for 4-5 days with daily medium changes to allow cells to polarize before using them in our assay.

To assay cellular toxicity, MTS assay (Promega™) was performed according to manufacturer instructions.

In Vivo Experiments:

Animal studies were approved by the Hospital for Sick Children Animal Care Committee with the regulation of the Canadian Council on Animal Care. Female Balb/C mice, age 6 to 8 weeks old were obtained from Charles River Laboratories (St. Constant, QC, Canada). Animals were kept in a specific pathogen free environment and fed food and water ad libitum.

For all intra-nasal instillation, lightly sedated mice (isoflurane) readily inhaled 50 μL of instillate applied to their nares with a P-200 pipetter while their mouth was held closed. On day 0 mice received $5\times10^6$ PFU of RSV via intranasal installation (n=4 to 6 per group). Mice were monitored and weighed daily.

For the AS1411 intraperitoneal (IP) injection, the methods were the same as for the intranasal instillations, with the exception of the AS1411 administration (standard mouse IP injection protocols were followed without sedation).

The RSV used (RSV-A2, ATCC) was amplified in HEp-2 cells and purified over sucrose in an ultracentrifuge.

On day 1, mice received AS-1411 via intranasal installation (at indicated dose; ranged from 10 mg/kg to 50 mg/kg) diluted in PBS. Control group received 50 mg/kg of CRO. In one experiment, AS-1411 administration was repeated on day 2 and 3. On day 4, mice were euthanized and the lungs removed, weighed and homogenized for viral titres. Titres were determined by standard plaque assay on HEp-2 cells.

The following examples are provide for illustrative purposes and are not intended to be limiting, as such:

EXAMPLES

Example 1

Figure 2:
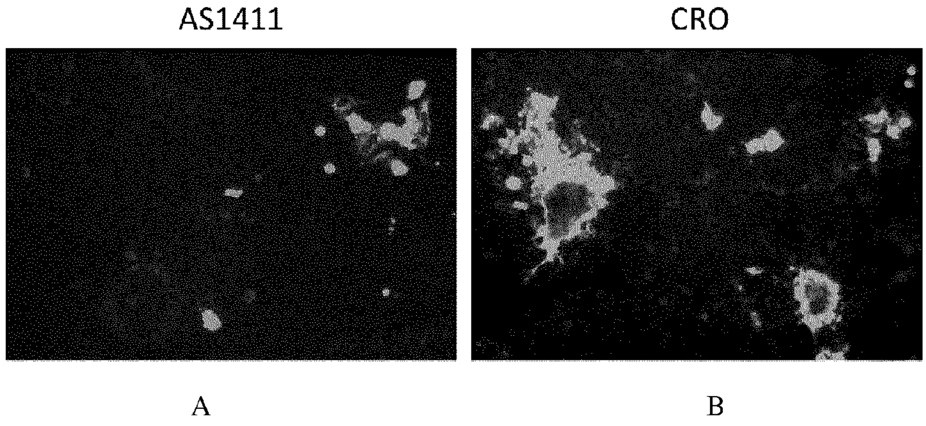
FIG. 2 shows representative fluorescence micrographs of HEp-2 cells from a therapeutic experiment treated with 17.5 μM AS1411 (panel A) and 17.5 μM CRO control (panel B), wherein the reduction in fluorescence signal is due to reduction in the overall number of infected cells (rather than a decreased amount of infection per cell).

Effect of Increased Concentration of AS1411 on Viral Infection of HEp-2 Cells In prophylactic experiments conducted over a wide dosing range of AS1411, the RSV-associated fluorescence signal was reduced by ~70%, without overt cytotoxicity (FIG. 1*a*; P=0.004). In therapeutic experiments we found that treating RSV-infected HEp-2 cell cultures with as little as 17.5 μM AS1411 resulted in a 50% decrease in fluorescence signal (FIG. 1*b*; P=0.0014), attributable to a reduction in the overall number of infected cells relative to the control (FIG. 2 panels A and B). Furthermore, CRO-treated control wells had more clusters of positive cells (FIG. 2, right panel B), indicative of cell-to-cell spread of RSV infection. These findings suggest that AS1411 acts in vitro not only to stop new infection events, but also to slow the spreading of infection outward from an initial focus of infection.

In both experiments (1 and 2—FIGS. 1*a* and 1*b*) 35 μM of AS1411 was sufficient to get a 60-70% decrease in fluorescent foci. In these experiments, the HEp-2 cells were pre-treated with the oligos for 24 hrs prior to adding the virus. Fluorescent foci where then detected 24 hrs after adding the virus.

Example 2

Figure 3:
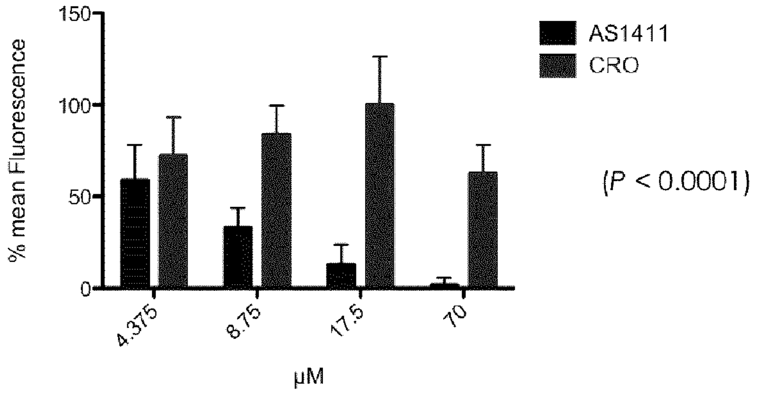
FIG. 3 shows a graph of the effect of increasing concentrations of AS1411 (left column) or CRO (right column) after RSV infection of MDCK cells (n=6; two-tailed paired t test), where the cells were exposed to RSV (MOI=0.1) 24 hrs prior to treating with AS1411/CRO and 17.5 μM and 70 μM of AS1411 was sufficient to get a 87% and 97% decrease in RSV fluorescence respectively, 24 hrs after addition to virus-infected MDCK cell cultures ($P<0.0001$).

Effect of Increased Concentration of AS1411 on Viral Infection of MDCK Cells Similar to EXAMPLE 1, the effect of increasing concentrations of AS1411 or CRO after RSV infection was tested on MDCK cells (therapeutic experiment; n=6; two-tailed paired t test). MDCK cells were exposed to RSV (MOI=0.1) 24 hrs prior to treating with AS1411/CRO. FIG. 3 shows that 17.5 μM and 70 μM of AS1411 is sufficient to get a 87% and 97% decrease in RSV fluorescence respectively, 24 hrs after addition to virus-infected MDCK cell cultures (P<0.0001).

Figure 4:
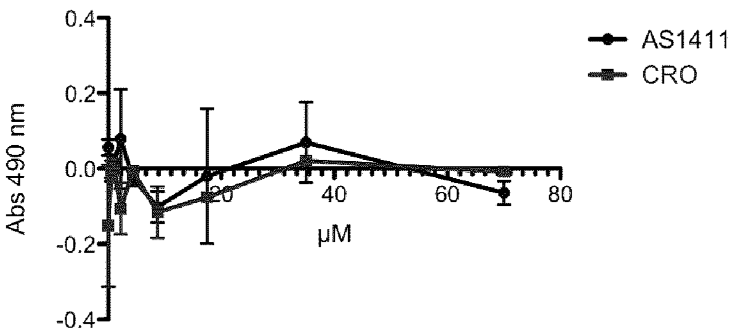
FIG. 4 shows the effect of increasing concentrations of AS1411 or CRO after RSV infection of MDCK cells in a therapeutic experiment, where MDCK cells were exposed to RSV (MOI=0.1) 24 hrs prior to treating with AS1411/CRO, and where an MTS assay was performed 24 hrs after treating with the oligos to assess cellular toxicity.

FIG. 4 shows the effect of AS1411 or CRO on MDCK cellular toxicity as measured by MTS assay (Promega™) performed 24 hrs after treating with the oligos. MDCK cells were exposed to RSV (MOI=0.1) 24 hrs prior to treating with AS1411/CRO. No difference is seen between AS1411 and CRO in terms of cellular proliferation and cellular health.

Figure 5:
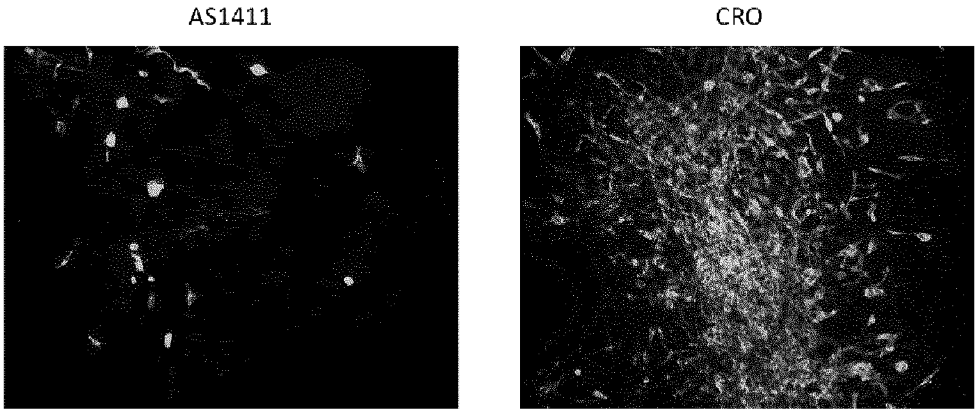
FIG. 5 shows fluorescence micrographs of representative cell culture wells from a therapeutic experiment with MDCK treated with 17.5 μM AS1411 (panel A) and 17.5 μM CRO control (panel B), wherein with the AS1411 treatment, the reduction in fluorescence signal is due to reduction in the overall number of infected cells.

FIG. 5 shows fluorescence images of cell culture wells from MDCK therapeutic experiment treated with 17.5 μM of AS1411 and CRO, respectively. As with FIG. 2, AS1411 treatment resulted in the reduction in fluorescence signal is due to reduction in the overall number of infected cells. Wells containing CRO show more clusters of virus-positive cells.

Example 3

Effect of AS1411 (Intranasal) on Viral Infection of Mouse Lung Tissue

Figure 6:
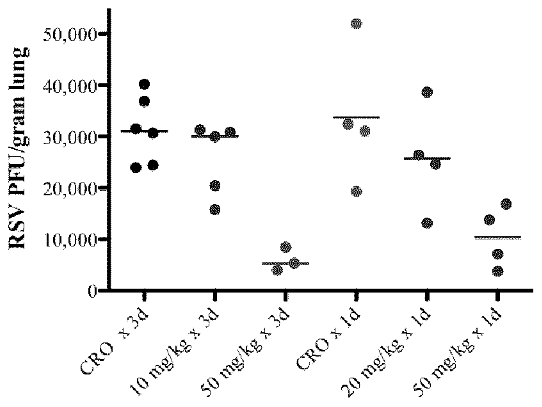
FIG. 6 shows a plot of RSV lung titers following AS1411 and a control oligo (CRO) delivery intranasally (at either 30 or 50 mg/kg and either 1 or 3 times per day) to mice who had received $5\times10^6$ PFU RSV on day 0 and either AS1411 or CRO starting day 1, when the mice were euthanized on day 4 RSV lung titres were determined.

AS1411 was also tested in live mice tissues to determine the effectiveness against RSV infection. FIG. 6 shows mice that were administered AS1411 or CRO delivered intranasally, following receipt of $5\times10^6$ PFU RSV on day 0 and treatment with AS1411 or CRO on day 1. Mice given AS1411 showed reduced RSV titres and repeated dosing had only a modest effect on lung titers. The mice given 50 mg/kg showed the most pronounced effect.

Figure 7:
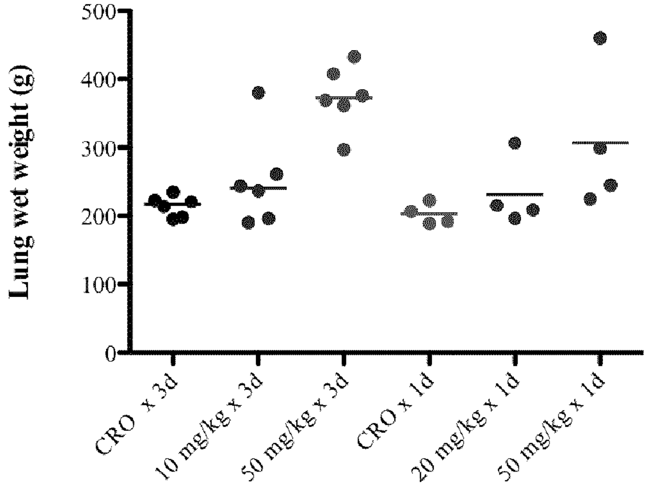
FIG. 7 shows a plot of lung weight for the same groups shown in FIG. 6, where the AS1411 groups had heavier and visibly redder lungs and no overt histopathology.
Figure 8:
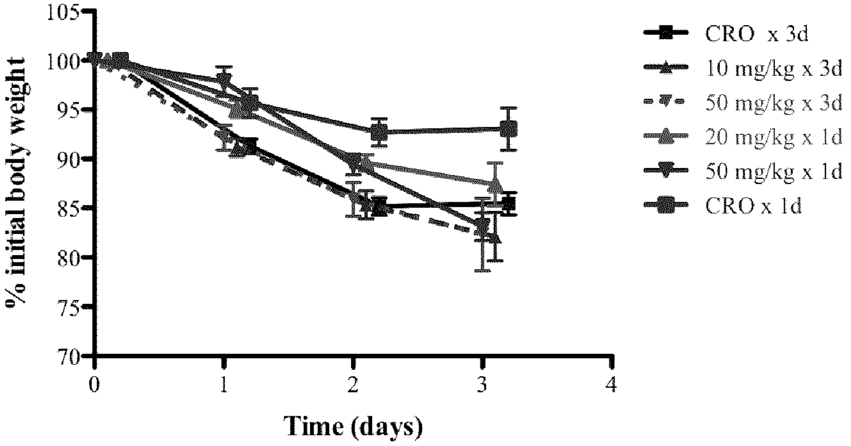
FIG. 8 shows a graph of % initial body weight for the same groups shown in FIG. 6, where the where the AS1411 is associated with less recovery of weight loss.

Furthermore, the AS1411 groups had heavier and visibly redder lungs, without any overt histopathology (FIG. 7). However, the AS1411 groups also were associated with less recovery of weight loss (see FIG. 8). In most cases, such body weight recovers when the animal recovers from the illness.

Figure 9:
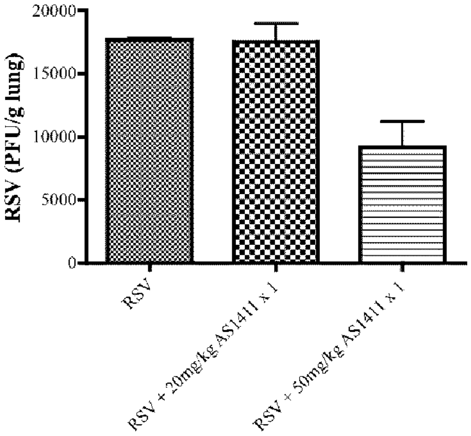
FIG. 9 shows a graph of RSV PFUs/g in lung tissue following treatment with clinical grade AS1411 delivered intranasally (single doses at 20 mg/kg and 50 mg/kg as compared to RSV alone).

The mouse experiment was repeated using clinical grade AS1411 (see FIG. 9—also, delivered intranasally) and showed results similar to those shown in FIG. 6.

TABLE 1

Tukey's Multiple Comparison Test:

| | Mean Diff. | Q | P value | 95% CI of diff |
|---|---|---|---|---|
| RSV vs RSV + 20 mg/kg AS1411 × 1 | 166.7 | 0.1662 | P > 0.05 | −4009 to 4343 |
| RSV vs RSV+ 50 mg/kg AS1411 × 1 | 8500 | 8.478 | P < 0.01 | 4324 to 12680 |
| RSV + 20 mg/kg AS1411 × 1 vs RSV + 50 mg/kg AS1411 × 1 | 8333 | 10.18 | P < 0.001 | 4924 to 11740 |

Figure 10:
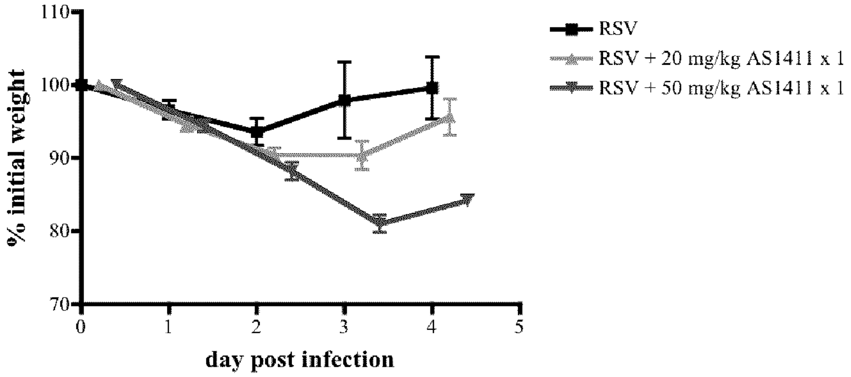
FIG. 10 shows a graph of % initial body weight for the same groups shown in FIG. 9, where the where the AS1411 is associated with less recovery of weight loss especially at 50 mg/kg.

Similarly, FIG. 10 shows that the % of initial weight is similar for clinical grade AS1411 as it is for non-clinical grade AS1411.

Example 4

Figure 11:
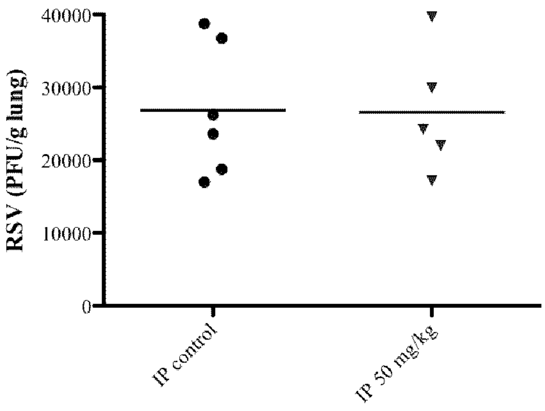
FIG. 11 shows a plot of RSV PFU/g in lung tissue following treatment with clinical grade AS1411 delivered by intraperitoneal injection (IP).

Effect of AS1411 (Intraperitoneal Injection (IP)) on Viral Infection of Mouse Lung Tissue For comparison purposes, FIG. 11 shows that IP injections of AS1411 (at 50 mg/kg) have no effect on RSV lung titers when compared to CRO control.

Although embodiments described herein have been described in some detail by way of illustration and example for the purposes of clarity of understanding, it will be readily apparent to those of skill in the art in light of the teachings described herein that changes and modifications may be made thereto without departing from the spirit or scope of the appended claims.

REFERENCES

Anderson et al. (1985). Antigenic characterization of respiratory syncytial virus strains with monoclonal antibodies. *J. Infect. Dis.* 151, 626-633.

Behera et al. (2001). Blocking intercellular adhesion molecule-1 on human epithelial cells decreases respiratory syncytial virus infection. *Biochem. Biophys. Res. Commun.* 280, 188-195.

Bem et al. (2009). Mechanical ventilation enhances lung inflammation and caspase activity in a model of mouse pneumovirus infection. *AJP—Lung Physiol.* 296, L46-L56.

Cane, P. A. and Pringle, C. R. (1995). Evolution of subgroup A respiratory syncytial virus: evidence for progressive accumulation of amino acid changes in the attachment protein. *J. Virol.* 69, 2918-2925.

Cane P. A. (1997). Analysis of linear epitopes recognised by the primary human antibody response to a variable region of the attachment (G) protein of respiratory syncytial virus. *J. Med. Virol.* 51, 297-304.

Cane, P. A. (2001). Molecular epidemiology of respiratory syncytial virus. *Rev. Med. Virol.* 11:103-116.

Chen et al. (2008). Cell surface nucleolin serves as receptor for DNA nanoparticles composed of pegylated polylysine and DNA. *Mol. Ther.* 16, 333-342.

Coates et al. (1966). An antigenic analysis of respiratory syncytial virus isolates by a plaque reduction neutralization test. *Am. J. Epidemiol.* 83, 299-313.

Collins, P. L. & Graham, B. S. (2008). Viral and host factors in human respiratory syncytial virus pathogenesis. *J Virol.* 82, 2040-2055.

Dapic, V. et al. (2002) Antiproliferative activity of G-quartet-forming oligonucleotides with backbone and sugar modifications. Biochemistry 41: 3676-85.

Dapic, V. et al. (2003) Biophysical and biological properties of quadruplex oligodeoxyribonucleotides. Nucleic Acids Res 31: 2097-107.

Domachowske, J. B. and Rosenberg, H. F. (1999). Respiratory syncytial virus infection: immune response, immunopathogenesis, and treatment. *Clinical Microbiol. Rev.* 12, 298-309.

Escobar, G. J., et al. (2010). Recurrent wheezing in the third year of life among children born at 32 weeks' gestation or later: relationship to laboratory-confirmed, medically attended infection with respiratory syncytial virus during the first year of life. *Arch. Pediatr. Adolesc. Med.* 164, 915-922.

Feldman et al. (2000). The fusion glycoprotein of human respiratory syncytial virus facilitates virus attachment and infectivity via an interaction with cellular heparan sulfate. *J. Virol.* 74, 6442-6447.

Garcia et al. (1994). Evolutionary patterns of human respiratory syncytial virus (subgroup A): cocirculating lineages and correlation of genetic and antigenic changes in the G glycoprotein. *J. Virol.* 68, 5448-5459.

Garcia-Barreno et al. (1989). Marked differences in the antigenic structure of human respiratory syncytial virus F and G glycoproteins. *J. Virol.* 63, 925-932.

Hall, C. B., et al. (2009). The burden of respiratory syncytial virus infection in young children. *N. Engl. J. Med.* 360, 588-598.

Hallak et al. (2000). Glycosaminoglycan sulfation requirements for respiratory syncytial virus infection. *J. Virol.* 74, 10508-10513.

Hallak, L. K., Kwilas, S. A. & Peeples, M. E. (2007). Interaction between respiratory syncytial virus and glycosaminoglycans, including heparan sulfate. *Methods Mol Biol* 379, 15-34.

Hendry et al. (1986). Concurrent circulation of antigenically distinct strains of respiratory syncytial virus during community outbreaks. *J. Infect. Dis.* 153, 291-297.

Johnson et al. (1987). The G glycoprotein of human respiratory syncytial viruses of subgroups A and B: extensive sequence divergence between antigenically related proteins. *Proc. Natl. Acad. Sci. USA* 84, 5625-5629.

Johnson et al. (2007). The histopathology of fatal untreated human respiratory syncytial virus infection. *Mod. Pathol.* 20, 108-119.

Kaan, P. M. and Hegele R. G. (2003). Interaction between respiratory syncytial virus and particulate matter in guinea pig alveolar macrophages. *Am. J. Respir. Cell. Mol. Biol.* 28, 697-704.

Krusat, T. and Streckert, H. J. (1997). Heparin-dependent attachment of respiratory syncytial virus (RSV) to host cells. *Arch. Virol.* 142, 1247-1254.

Malhotra et al. (2003). Isolation and characterisation of potential respiratory syncytial virus receptor(s) on epithelial cells. *Microbes Infect* 5, 123-133.

Marsh, M. and Helenius, A. (2006). Virus Entry: Open Sesame. *Cell* 124, 729-740.

Mufson et al. (1985). Two distinct subtypes of human respiratory syncytial virus. *J. Gen. Virol.* 66, 2111-2124.

Nisole et al. (1999). The anti-HIV pseudopeptide HB-19 forms a complex with the cell-surface-expressed nucleolin independent of heparan sulfate proteoglycans. *J. Biol. Chem.* 274, 27875-84.

Peret et al. (1998). Circulation patterns of genetically distinct group A and B strains of human respiratory syncytial virus in a community. *J. Gen. Virol.* 79, 2221-2229.

Rueda et al. (1991). Premature stop codons in the G glycoprotein of human respiratory syncytial viruses resistant to neutralization by monoclonal antibodies. *J. Virol.* 65, 3374-3378.

Sullender et al. (1991). Genetic diversity of the attachment protein of subgroup B respiratory syncytial viruses. *J. Virol.* 65, 5425-5434.

Sullender et al. (1993). Analysis of respiratory syncytial virus genetic variability with amplified cDNAs. *J. Clin. Microbiol.* 31, 1224-1231.

Tayyari, F. et al. (2011). Identification of nucleolin as a cellular receptor for human respiratory syncytial virus. Nat Med. 17(9):1132-5.

Techaarpornkul, S., Barretto, N. & Peeples, M. E. (2001). Functional analysis of recombinant respiratory syncytial virus deletion mutants lacking the small hydrophobic and/or attachment glycoprotein gene. *J. Virol.* 75, 6825-6834.

Techaarpornkul, S., Collins, P. L. & Peeples, M. E. (2002). Respiratory syncytial virus with the fusion protein as its only viral glycoprotein is less dependent on cellular glycosaminoglycans for attachment than complete virus. *Virology* 294, 296-304.

Tuteja et al. (1998). Nucleolin: a multifunctional major nucleolar phosphoprotein. *Crit. Rev. Biochem. Mol. Biol.* 33, 407-436.

Wu, H., Pfarr, D. S., Losonsky, G. A. & Kiener, P. A. (2008). Immunoprophylaxis of RSV infection: advancing from RSV-IGIV to palivizumab and motavizumab. *Curr Top Microbiol Immunol* 317, 103-123.

Zhang, L., Peeples, M. E., Boucher, R. C., Collins, P. L. & Pickles, R. J. (2002). Respiratory syncytial virus infection of human airway epithelial cells is polarized, specific to ciliated cells, and without obvious cytopathology. *J Virol* 76, 5654-5666.

```
INFORMAL SEQUENCE LISTINGS
SEQ ID NO: 1: Description: AS1411
  1 GGTGGTGGTG GTTGTGGTGG TGGTGG 26

SEQ ID NO: 2: Description: human nucleolin
  1 MVKLAKAGKN QGDPKKMAPP PKEVEEDSED EEMSEDEEDD SSGEEVVIPQ KKGKKAAATS

 61 AKKVVVSPTK KVAVATPAKK AAVTPGKKAA ATPAKKTVTP AKAVTTPGKK GATPGKALVA
```

-continued

121 TPGKKGAAIP AKGAKNGKNA KKEDSDEEED DDSEEDEEDD EDEDEDEDEI EPAAMKAAAA

181 APASEDEDDE DDEDDEDDDD DEEDDSEEEA METTPAKGKK AAKVVPVKAK NVAEDEDEEE

241 DDEDEDDDDD EDDEDDDDED DEEEEEEEEE EPVKEAPGKR KKEMAKQKAA PEAKKQKVEG

301 TEPTTAFNLF VGNLNFNKSA PELKTGISDV FAKNDLAVVD VRIGMTRKFG YVDFESAEDL

361 EKALELTGLK VFGNEIKLEK PKGKDSKKER DARTLLAKNL PYKVTQDELK EVFEDAAEIR

421 LVSKDGKSKG IAYIEFKTEA DAEKTFEEKQ GTEIDGRSIS LYYTGEKGQN QDYRGGKNST

481 WSGESKTLVL SNLSYSATEE TLQEVFEKAT FIKVPQNQNG KSKGYAFIEF ASFEDAKEAL

541 NSCNKREIEG RAIRLELQGP RGSPNARSQP SKTLFVKGLS EDTTEETLKE SFDGSVRARI

601 VTDRETGSSK GFGFVDFNSE EDAKAAKEAM EDGEIDGNKV TLDWAKPKGE GGFGGRGGGR

661 GGFGGRGGGR GGRGGFGGRG RGGFGGRGGF RGGRGGGGDH KPQGKKTKFE

SEQ ID NO: 3: Description: CRO
1 CCTCCTCCTC CTTCTCCTCC TCCTCC 26

What is claimed is:

1. A method of treating respiratory syncytial virus (RSV) infection in a cell of a subject, the method comprising administering AS1411 (SEQ ID NO:1) to the cell via intranasal administration to the subject.

2. The method of claim 1, wherein the cell is a human cell.

3. The method of claim 2, wherein the human cell is an epithelial cell.

4. The method of claim 2, wherein the human cell is a ciliated respiratory epithelial cell.

5. The method of claim 1, wherein the subject is a human having or at risk of developing an RSV infection.

6. The method of claim 1, wherein AS1411 is mixed with lipid particles prior to administration.

7. The method of claim 1, wherein AS1411 is encapsulated in liposomes prior to administration.

8. A method of treating respiratory syncytial virus (RSV) infection in a human ciliated respiratory epithelial cell, which cell is in a human subject having or at risk of developing an RSV infection, the method comprising intranasally administering AS1411 (SEQ ID NO:1) to the subject.

9. The method of claim 8, wherein AS1411 is mixed with lipid particles prior to administration.

10. The method of claim 8 wherein AS1411 is encapsulated in liposomes prior to administration.

* * * * *